US00PP32323P2

(12) United States Plant Patent
Hansen

(10) Patent No.: US PP32,323 P2
(45) Date of Patent: Oct. 13, 2020

(54) ***PHLOX* PLANT NAMED 'COVER GIRL'**

(50) Latin Name: *Phlox paniculata*
Varietal Denomination: Cover Girl

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,088

(22) Filed: Jan. 30, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A new and unique hybrid cultivar of *Phlox* plant named *Phlox* 'Cover Girl' of tall, multi-stemmed, upright habit. Foliage is thick, with exceptional powdery mildew resistance on stiff stems. Lavender-purple are produced on large heads of branched peduncles and nearly cover the top of the plant beginning mid-July and continuing and reblooming for about seven weeks through late summer. 'Cover Girl' is especially suitable as a potted plant, for the garden, for attracting hummingbirds and butterflies, and for cut flower arrangements.

1 Drawing Sheet

Botanical classification: *Phlox paniculata.*
Variety denomination: 'Cover Girl'.

STATEMENT REGARDING PRIOR DISCLOSURES UNDER 37 CFR 1.77(B)(6)

The first non-enabling disclosure, in the form of a website with a photograph and brief description was on Feb. 1, 2019 maintained by Walters Gardens, Inc. Subsequently, Walters Gardens, Inc. published an advertisement in their "Walters Gardens 19-20 Catalog" on May 29, 2019, and first sold the new plant on Jul. 8, 2019. Walters Gardens, Inc. obtained the new plant and all information relating thereto, from the inventor. No plants of *Phlox* 'Cover Girl' have been sold, in this country or anywhere in the world, under this or any name, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct Tall *Phlox* cultivar of *Phlox* plant, known as *Phlox* 'Cover Girl' and will be referred to hereafter by its cultivar name or the "new plant". The new plant was the result of a controlled pollination of the proprietary, unreleased, hybrid known only as 2013 PHL AA-2 (not patented) as the female or seed parent and the proprietary, unreleased hybrid known as 2013 PHL-14-AA (not patented) as the male or pollen parent. The cross was performed by the inventor on Aug. 7, 2014 in the greenhouses at a wholesale perennial nursery in Zeeland, Mich., and seed was collected in the autumn of 2015. During the trial process the new plant arising as a single seedling selection from the identified cross was identified by the breeder code 14-598-1. 'Cover Girl' has been asexually propagated by tip and basal stem cuttings in the greenhouses at the same nursery in Zeeland, Mich. since 2016, as well as by shoot tip tissue culture. The unique characteristics of the new plant have been found to be reproducible and stable in successive generations of asexually propagated plants and the resultant plants have been found to be identical to the original selection.

BRIEF SUMMARY OF THE PLANT

*Phlox* 'Cover Girl' is unique from its parents and all other tall garden *Phlox* or other hybrid *Phlox* known to the inventor. The closest comparison cultivars known to the inventor are 'Barfourteen' U.S. Plant Pat. No. 12,605 and 'Balkapopur' U.S. Plant Pat. No. 30,781. 'Barfourteen' and 'Balkapopur' are both much shorter in habit and have a slightly more reddish hue of the flower face. Compared with 'Glamour Girl' U.S. Plant Pat. No. 25,778 the new plant is slightly taller and 'Glamour Girl' has flowers that are more hot coral pink. Copending U.S. Plant patent application Ser. No. 16/873,087 'Party Girl' has a slightly shorter habit and white flowers with a star-shaped light pink centers made up of two spots per petal. Copending U.S. Plant Patent Application 'Uptown Girl' has a slightly short habit with flowers that are light pinkish lavender with a darker center.

'Cover Girl' differs from all other *Phlox* known to the inventor in the following repeatedly observed traits in combination:

1. Tall plants of upright habit, producing clean, medium-green, lanceolate leaves;
2. Showing exceptional powdery mildew resistance;
3. Multiple stems produce large branched mounds of flowers starting in mid-July for about seven weeks;
4. Flowers on strong stiff stems of just over a meter tall producing lavender-purple flower;
5. Flowers cover nearly the entire top of the plant;

BRIEF DESCRIPTION OF THE DRAWINGS

The photographs of the new plant demonstrate the unique traits of 'Cover Girl' and the overall appearance of three-year-old plants grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
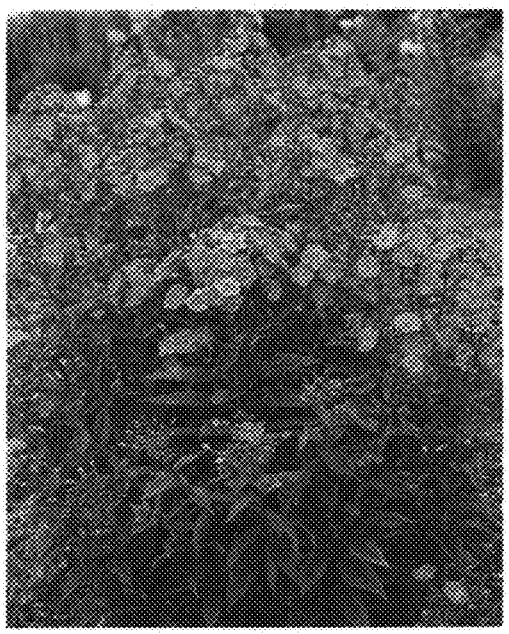
FIG. 1 shows the habit of the new plant just beginning to flower in the landscape.
Figure 2:
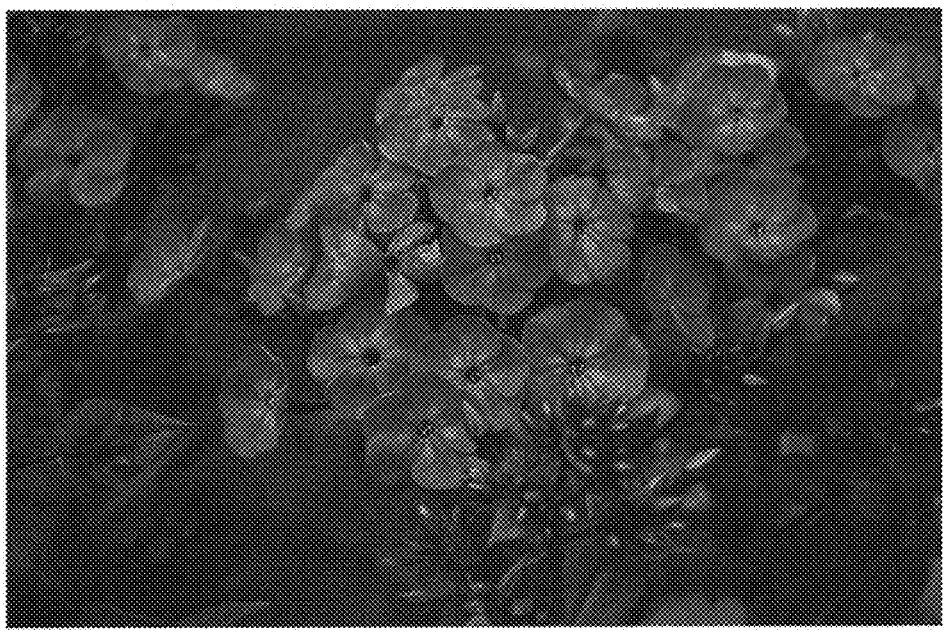
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Cover Girl' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full sun garden of a wholesale perennial nursery in Zeeland, Mich. with supplemental fertilizer and water as needed.

Botanical classification: *Phlox paniculata;*

Parentage: 2013 PHL AA-2 as the female or seed parent and presumably either the proprietary, unreleased hybrid known as 2013 PHL-14-AA as the male or pollen parent;

Plant habit: Hardy herbaceous perennial, densely upright, producing about 28 rigid mostly upright stems; flowering at up to 108.0 cm tall and about 80.0 cm wide; flowering begins mid-July in Michigan and continuing for about 7 weeks with repeating into late summer;

Propagation: Stem cuttings; rooting in about 21 days;

Time to produce finished crop in 3.8 liter pots: About 10 to 12 weeks from a 25 mm liner; moderate rate of growth;

Root: Primary roots to about 1.0 mm thick; secondary fibrous and freely branching; color creamy white to tan depending on soil type; color of active roots nearest RHS NN155B depending on soil components;

Leaves: Simple; opposite; ovoid; acute apex; rounded to truncate base; sessile; entire margin; tough, coriaceous;

Leaf size: To about 14.0 cm long by about 45.0 mm wide; average about 12.7 cm long by about 32.0 mm wide; becoming smaller distally;

Leaf surfaces: Glabrous and lustrous adaxial, glabrous and matte abaxial;

Leaf color expanding: Adaxial nearest RHS 146C, abaxial nearest RHS 138B;

Leaf color at flowering: Adaxial between RBS NN137B and RHS 137A, abaxial between RHS 146B and RHS 138B;

Foliage fragrance: None detected;

Veins: Pinnate; glabrous adaxial and abaxial; midrib about 1.5 mm wide at base, slightly sunken adaxial and raised abaxial;

Vein color: Adaxial midrib nearest RHS 146D and lateral veins between RHS 146D and RHS 151D, abaxial midrib nearest RHS 145C and laterally nearest RHS 146D;

Petiole: Leaves sessile;

Stems: About 28 per plant; cylindrical; stiff; wiry; strong; mostly upright; glabrous; to about 108.0 cm long and 10 mm diameter at base, average about 100.0 cm long and 8.0 mm diameter at base;

Stem color: Nearest RHS 146D;

Nodes: About 18 per stem below initial flowers plus 12 nodes in branched flower head; average internode length about 4.5 cm;

Node color: Nearest RHS 146D;

Inflorescence: A loosely-branched compound corymb of about 100 flowers; initial flowering portion about 20.0 cm long and 16.0 cm across;

Flowers: Perfect; salverform with flat face and long fused tube; actinomophic; typically with five petals; about 24.0 mm long total with tube about 22.0 mm long and 2.5 mm diameter at base and 5.0 mm diameter below face; face about 30.0 mm across; attitude upright to slightly outward; self-cleaning;

Flower longevity: Individually about 5 days on plant or as cut flower;

Flower fragrance: Lightly sweet;

Buds one to two days prior to opening: Narrowly oblanceolate, to nearly clavate; acute apex with petals implicate about each other; base fused; total bud about 19.0 mm long, tube about 12.0 mm long and 2.5 mm diameter in tube, bulb 7.0 mm long and swollen to 5.0 mm diameter toward apex of convolute petals;

Bud color: Petals nearest RHS 83D in bulb and nearest RHS N77B in corolla tube;

Petals: Five; sympetalous; margin entire; apex rounded; base fused into tube; abaxial and adaxial limb glabrous, abaxial tube surface puberulent, adaxial corolla pubescent between 4 mm and 8 mm from base; limbs strongly imbricate, about 40 percent over the next petal;

Petal size: Limb to about 14.0 mm wide and about 12.0 mm long, corolla tube to about 22.0 mm long and 2.5 mm diameter at base and 5.0 mm diameter at face;

Petal color: (Young) adaxial limb between RHS N78A and RHS N78B with two longitudinal marks about 3 mm long in center eye nearest RHS 69C; abaxial limb nearest RHS N81D and margin nearest RHS N78A; adaxial corolla tube basal 2.0 mm nearest RHS NN155D, distally nearest RHS 70A; abaxial corolla tube basal 2.0 mm nearest RHS NN155D, distally nearest RHS 70A;

Petal color: (Mature) adaxial limb between RHS 72B and RHS N74C, adaxial corolla tube basal 2.0 mm nearest RHS NN155D, distally nearest RHS 70A; abaxial limb nearest RHS 76B, corolla tube nearest RHS NN155D in basal 2.0 mm and distally nearest RHS 70A;

Androecium: Five;

*Filaments*.—Typically five; straight; cylindrical; adnate to adaxial corolla tube except free in distal 0.5 mm; varying lengths between 14.0 mm and 18.0 mm, about 0.2 mm in diameter; color nearest RHS NN155D.

*Anther*.—Five; oblong elliptic; dorsifixed; longitudinal; about 3.0 mm long by 1.0 mm wide; color nearest RHS 4D.

*Pollen*.—Abundant; color nearest RHS 9D.

Gynoecium: One pistil per flower; to about 21.5 mm long;

*Style*.—Cylindrical; straight; about 18.0 mm long and about 0.3 mm diameter; persistent after flower abscission; color nearest RHS N186D.

*Stigma*.—Trifid in the distal 1.0 mm, about 0.3 mm in diameter; color nearest RHS 155A.

*Ovary*.—Superior; conical; acute apex, base truncate; about 2.5 mm long and 1.0 mm diameter; color nearest RHS 144A.

Calyx: Tubular; adpressed to corolla tube; to about 9.0 mm long and 4.0 mm cross at apex;

Sepals: Five; linear; narrowly acute apex, margin entire; basal 4.0 mm fused; abaxial surface matte and adaxial slightly lustrous; persistent; individually about 9.0 mm long and 1.5 mm wide;

Sepal color: Adaxial nearest RHS 146B with fine spotting of nearest RHS N186C, margin translucent nearest RHS N77D; abaxial nearest RHS N77A with margins nearest RHS NN155B;

Peduncle: Glabrous, stiff, strong, moderately lustrous, upright, cylindrical; flowering portion average about 20.0 cm long, and 4.0 mm diameter at base of flower branches; branches to about 16.0 mm long and 2.5 mm diameter at base;

Peduncle color: Nearest blend of RHS 145A and RHS 146D with strong blush of nearest RHS 187C in regions or high light intensity;

Bracts: Subtending upper branches and flowers; lanceolate; ciliolate margin; acute apex; sessile truncate base; glabrous; to about 4.0 cm long and 10.0 mm across;

Bract color: Same as leaves in both adaxial and abaxial surfaces;

Pedicel: Cylindrical; glabrous; to about 4.0 mm long and 1.0 mm diameter;

Pedicel color: Nearest RHS 146D maculate with nearest RHS 186C;

Fruit and seeds have not yet been observed.

Hardiness and culture: The new plant grows best with plenty of moisture and adequate drainage; hardy to at least from USDA zone 4 through 8.

Disease and pest resistance: *Phlox* 'Cover Girl' demonstrated the excellent powdery mildew resistance caused by *Erysiphe cichoracearum* in the presence and under conditions of intense pressure that would normally show symptoms.

I claim:

1. A new and distinct cultivar of hybrid *Phlox* plant named *Phlox* 'Cover Girl', as herein described and illustrated.

* * * * *